United States Patent [19]
Campbell et al.

[11] Patent Number: 6,159,565
[45] Date of Patent: *Dec. 12, 2000

[54] THIN-WALL INTRALUMINAL GRAFT

[75] Inventors: Carey V. Campbell; James D. Lewis, both of Flagstaff; David J. Myers, Camp Verde, all of Ariz.

[73] Assignee: W. L. Gore & Associates, Inc., Newark, Del.

[ * ] Notice: This patent is subject to a terminal disclaimer.

[21] Appl. No.: 08/108,963

[22] Filed: Aug. 18, 1993

[51] Int. Cl.⁷ ................................................. B29D 22/00
[52] U.S. Cl. .................... 428/35.7; 428/36.9; 428/36.91; 428/36.92; 428/420; 428/421; 428/422; 623/1
[58] Field of Search .............................. 623/1; 428/35.7, 428/36.9, 36.91, 36.92, 420, 421, 422

[56] References Cited

U.S. PATENT DOCUMENTS

| | | |
|---|---|---|
| 3,657,744 | 4/1972 | Ersek . |
| 3,868,956 | 3/1975 | Alfidi et al. . |
| 3,953,566 | 4/1976 | Gore . |
| 4,055,696 | 10/1977 | Kamada et al. . |
| 4,130,904 | 12/1978 | Whalen . |
| 4,140,126 | 2/1979 | Choudury . |
| 4,190,909 | 3/1980 | Ablaza . |
| 4,250,138 | 2/1981 | Okita . |
| 4,313,231 | 2/1982 | Koyamada . |
| 4,347,204 | 8/1982 | Takagi et al. . |
| 4,478,898 | 10/1984 | Kato . |
| 4,512,228 | 4/1985 | Balko et al. . |
| 4,553,545 | 11/1985 | Maass et al. . |
| 4,562,596 | 1/1986 | Kornberg . |
| 4,577,631 | 3/1986 | Kreamer . |
| 4,598,011 | 7/1986 | Bowman ................................ 428/221 |
| 4,655,771 | 4/1987 | Wallsten . |
| 4,681,110 | 7/1987 | Wiktor . |
| 4,713,070 | 12/1987 | Mano . |
| 4,776,337 | 10/1988 | Palmaz . |
| 4,787,899 | 11/1988 | Lazarus . |
| 4,791,966 | 12/1988 | Eilentropp . |
| 4,820,298 | 4/1989 | Leveen et al. . |
| 4,822,361 | 4/1989 | Okita et al. . |
| 4,877,030 | 10/1989 | Beck et al. . |
| 4,877,661 | 10/1989 | House et al. ............................ 428/34.9 |
| 4,878,906 | 11/1989 | Lindemann et al. . |
| 4,925,710 | 5/1990 | Buck et al. . |
| 4,954,126 | 9/1990 | Wallsten . |
| 5,024,671 | 6/1991 | Tu et al. ..................................... 623/1 |
| 5,078,726 | 1/1992 | Kreamer . |
| 5,107,852 | 4/1992 | Davidson et al. . |
| 5,122,154 | 6/1992 | Rhodes . |
| 5,123,917 | 6/1992 | Lee . |
| 5,151,105 | 9/1992 | Kwan-Gett . |
| 5,156,620 | 10/1992 | Pigott . |
| 5,211,658 | 5/1993 | Clouse . |
| 5,225,131 | 7/1993 | Tamaru . |
| 5,236,447 | 8/1993 | Kubo et al. . |
| 5,288,552 | 2/1994 | Hollewbangn Jr. et al. ........... 428/357 |

FOREIGN PATENT DOCUMENTS

| | | |
|---|---|---|
| 461791 | 12/1991 | European Pat. Off. . |
| 464755 | 1/1992 | European Pat. Off. . |
| 466518 | 1/1992 | European Pat. Off. . |
| 480667 | 4/1992 | European Pat. Off. . |
| 508473 | 10/1992 | European Pat. Off. . |
| 518704 | 12/1992 | European Pat. Off. . |
| 528039 | 2/1993 | European Pat. Off. . |
| 539237 | 4/1993 | European Pat. Off. . |
| 3918736 | 12/1990 | Germany . |
| 5536492 | 5/1976 | Japan . |
| 53-67109 | 6/1978 | Japan . |
| 60-172306 | 9/1985 | Japan . |
| 9112779 | 9/1991 | WIPO . |
| 9113648 | 9/1991 | WIPO . |

OTHER PUBLICATIONS

Balko A et al., Transfemoral Placement of Intraluminal Polyurethane Prosthesis for Abdominal Aortic Aneurysm. Jou of Surg Research 1986; 40:305–309.

Chuter T A M et al., Transfemoral Endovascular Aortic Graft Placement. Jour of Vas Surg Aug. 1993; vol. 18 (2):185–197.

Cragg A H, Drake M D. Percutaneous Femoropopliteal Graft Placement. Radiology 1993; 187(3):643–648.

George P J M et al., Covered expandable metal stent for recurrent tracheal obstruction. The Lancet, Mar. 1990; 335:582–584.

Kato M et al., Development of a chronic endothelialized transcatheter implantable intra–aortic graft. ASAIO Journal 1993; M518–M521.

Lawrence D D et al., Percutaneous Endovascular Graft: Experimental Evaluation. Radiology May 1987; 163(2):357–360.

Mirich D et al., Percutaneously Placed Endovascular Grafts for Aortic Aneurysms: Feasibility Study. Radiology 1989; 170(3):1033–1037.

(List continued on next page.)

*Primary Examiner*—Michael P. Woodward
*Assistant Examiner*—Patrick R. Delaney
*Attorney, Agent, or Firm*—Wayne D. House

[57] ABSTRACT

An intraluminal vascular graft in the form of a tube of porous expanded polytetrafluoroethylene film wherein the porous polytetrafluoroethylene film has a microstructure containing a multiplicity of fibrils oriented substantially parallel to each other. The tube has a wall thickness of less than about 0.25 mm and is made from at least one first layer and at least one second layer of porous polytetrafluoroethylene film, wherein the fibrils of the first and second layers are oriented substantially perpendicular to each other. Preferably the fibrils of the at least one first layer are oriented substantially parallel to the longitudinal axis of the tube and the fibrils of the at least one second layer of porous polytetrafluoroethylene film are oriented substantially circumferential to the tube. The first and second layers may be inner and outer layers respectively, or alternatively their relationship may be reversed. Alternatively, either of the first and second film layers may be replaced with alternative reinforcing components such as a braid or at least one reinforcing rib.

26 Claims, 6 Drawing Sheets

OTHER PUBLICATIONS

Parodi J C et al., Transfemoral Intraluminal Graft Implantation for Abdominal Aortic Aneurysms. Annals of Vascular Surg 1991; vol. 5(6):491–499.

Preminger T J et al., Transluminal vascular stenting using a GORE–TEX covered stent: An experimental study. Presented at the congress of Pediatric Cardiology and Cardiac Surgery Jun. 21–25 1993.

Sayers R D et al., Endovascular stenting of abdominal aortic aneurysms. Eur J Vasc Surg 1993; 7:225–227.

Schenck R R and Derman G H. An Intraluminal Silastic Stent for Small Vessel Repair. Orth Clin North Amer. Apr. 1977; 8(2):265–271.

Yoshida H et al., Transcatheter Placement of an Intraluminal Prosthesis for the Thoracic Aorta, A New Approach to Aortic Dissections. ASAIO Transactions 1991; 37:M272–M273.

Yoshioka T et al. Self–Expanding Endovascular Graft: An Experimental Study in Dogs. AJR Oct. 1988; 151:673–676.

Notice of Opposition to European Patent EP 714,487 to W. L. Gore & Assoc., Inc by Meadox Medicals Inc. (including Facts and Arguments)(Jan. 21, 1999.).

THIN-WALL INTRALUMINAL GRAFT

FIELD OF THE INVENTION

This invention relates to the field of intraluminal grafts and particularly to thin-wall intraluminal grafts useful as a lining for blood vessels or other body conduits.

BACKGROUND OF THE INVENTION

Conventional vascular grafts have long been used for vascular repair in humans and animals. These devices are typically flexible tubes of woven or knitted polyethylene terephthalate or of porous polytetrafluoroethylene (hereinafter PTFE). Grafts of biological origin are also used, these being typically fixed human umbilical or bovine arteries. These conventional vascular grafts usually require invasive surgical methods that expose at least both ends of the segment of vessel to be repaired. Frequently it is necessary to expose the entire length of the vessel segment. These types of repairs consequently cause major trauma to the patient with corresponding lengthy recovery periods and may result in occasional mortality.

Alternative methods have evolved which use intraluminal vascular grafts in the form of diametrically-expandable metallic stent structural supports, tubular grafts or a combination of both. These devices are preferably remotely introduced into a body cavity by the use of a catheter type of delivery system. Alternatively they may be directly implanted by invasive surgery. The intent of these methods is to maintain patency after an occluded vessel has been re-opened using balloon angioplasty, laser angioplasty, atherectomy, rotoablation, invasive surgery, or a combination of these treatments.

Intraluminal vascular grafts can also be used to repair aneurysmal vessels, particularly aortic arteries, by inserting an intraluminal vascular graft within the aneurysmal vessel so that the prosthetic withstands the blood pressure forces responsible for creating the aneurysm.

Intraluminal vascular grafts provide a new blood contacting surface within the lumen of a diseased living vessel. Intraluminal grafts are not, however, limited to blood vessels; other applications include urinary tracts, biliary ducts, respiratory tracts and the like.

If the intraluminal graft used is of thin enough wall and adequate flexibility, it may be collapsed and inserted into a body conduit at a smaller diameter location remote from the intended repair site. A catheter type of delivery system is then used to move the intraluminal graft into the repair site and then expand its diameter appropriately to conform to the inner surface of the living vessel. Various attachment methods including the use of expandable metallic stents may be used to secure the intraluminal graft at the desired location while requiring only minimally invasive surgery.

Intraluminal vascular grafts were suggested as early as 1912 in an article by Alexis Carrel (Results of the permanent intubation of the thoracic aorta. Surg., Gyn and Ob. 1912;15:245–248). U.S. Pat. No. 3,657,744 to Ersek describes a method of using one or more expandable stents to secure a flexible fabric vascular graft intraluminally, the graft and stent having been introduced distally and delivered to the desired position with a separate delivery system.

Choudhury, U.S. Pat. No. 4,140,126, describes a similar method of repairing aortic aneurysms whereby a polyethylene terephthalate vascular graft is fitted at its ends with metal anchoring pins and pleated longitudinally to collapse the graft to a size small enough to allow for distal introduction.

Rhodes, U.S. Pat. No. 5,122,154 and Lee, U.S. Pat. No. 5,123,917, describe endovascular bypass grafts for intraluminal use which comprise a sleeve having at least two diametrically-expandable stents. Rhodes teaches that the sleeve material is to be made of conventional vascular graft materials such as GORE-TEX® Vascular Graft (W. L. Gore & Associates, Inc., Flagstaff, Ariz.) or Impra® Graft (Impra, Inc., Tempe, Ariz.). Both the GORE-TEX Vascular Graft and Impra Graft are extruded and longitudinally expanded PTFE tubes. Additionally, the GORE-TEX Vascular Graft possesses an exterior helical wrapping of porous expanded PTFE film. The difficulty with the use of either the GORE-TEX Vascular Graft or the Impra Graft as the sleeve component is that the relatively thick, bulky wall of the extruded, longitudinally expanded PTFE tubes limits the ability of the tube to be contracted into a small cross-sectional area for insertion into a blood vessel. For example, the wall thickness of a 6 mm inside diameter Thin Walled GORE-TEX Vascular Graft is typically 0.4 mm. The thinness of the wall is limited by the difficulty of producing an extruded, longitudinally expanded tube having a thin wall of uniform thickness.

SUMMARY OF THE INVENTION

The present invention is a tubular intraluminal graft comprising a tube of porous expanded PTFE film wherein the porous expanded PTFE film has a microstructure containing a multiplicity of fibrils oriented substantially parallel to each other. The tube has a wall thickness of less than about 0.25 mm and preferably less than 0.1 mm wherein the tube comprises a first layer of porous expanded PTFE film and a second layer of porous expanded PTFE film wherein the fibrils of the first layer of porous expanded PTFE film are oriented perpendicular to the fibrils of the second layer of porous expanded PTFE film. More preferably the fibrils of the first layer of porous expanded PTFE film are oriented substantially parallel to the longitudinal axis of the tube and the fibrils of the second layer of porous PTFE film are oriented substantially circumferential to the tube.

The term expanded is used herein to refer to porous expanded PTFE. The terms expand, expanding and expandable are used herein to refer to diametrically-adjustable intraluminal stents.

The first layer is preferably the inner layer with the second layer serving as an outer layer. Alternatively, the relationship between the first and second layers may be reversed so that the second layer serves as the inner layer of the graft.

The inventive intraluminal graft has good hoop strength when exposed to blood pressure because of the circumferentially oriented layers of film. The graft is flexible and collapsible, thereby allowing it to be collapsed to a size much smaller than the full inside diameter. The graft is capable of being implanted into a living body in the collapsed state and can therefore be inserted into a conveniently accessible, smaller diameter portion of a body conduit and then transferred to another, larger diameter portion of the body conduit where it is needed with the use of a catheter type of delivery system. One end of the intraluminal graft is then secured by suitable means such as the use of one or more metallic expandable stents. The use of the inventive intraluminal graft thus allows for the effective repair of living blood vessels without the trauma typically associated with conventional invasive vascular surgery.

The inventive intraluminal graft may optionally incorporate separate longitudinally-oriented ribs intended to serve as additional strength members. These ribs may be in the form of, for example, stringers of PTFE or fluorinated ethylene propylene (hereinafter FEP) of small diameter such as about 0.025 mm to about 0.5 mm. The use of such longitudinally-oriented ribs can add significantly to the longitudinal strength of the graft without appreciably interfering with the ability of the graft to be collapsed in diameter for ease of insertion into a vascular system and then subsequently increased in diameter at a different location within the vascular system. These ribs may easily be incorporated into the graft during construction of the graft, for example, by temporarily attaching the ribs to the surface of a manufacturing mandrel prior to wrapping the mandrel with a layer of porous expanded PTFE film. The mandrel assembly can then be heated adequately to cause the ribs to adhere to the film, after which the mandrel can be removed. The ribs may be located on the luminal surface of the film, on the exterior surface of the film, or between two layers of the film.

Alternatively, either the first or second film layers may be replaced by alternative reinforcing components such as a braid or at least one reinforcing rib. If at least one reinforcing rib is used, the at least one rib should be oriented to be substantially perpendicular to the fibrils of the remaining film layer.

DETAILED DESCRIPTION OF THE INVENTION

The porous expanded PTFE film from which the vascular graft of the present invention is constructed is made as taught by U.S. Pat. Nos. 3,953,566 and 4,187,390. These patents are herein incorporated by reference.

Figure 1:
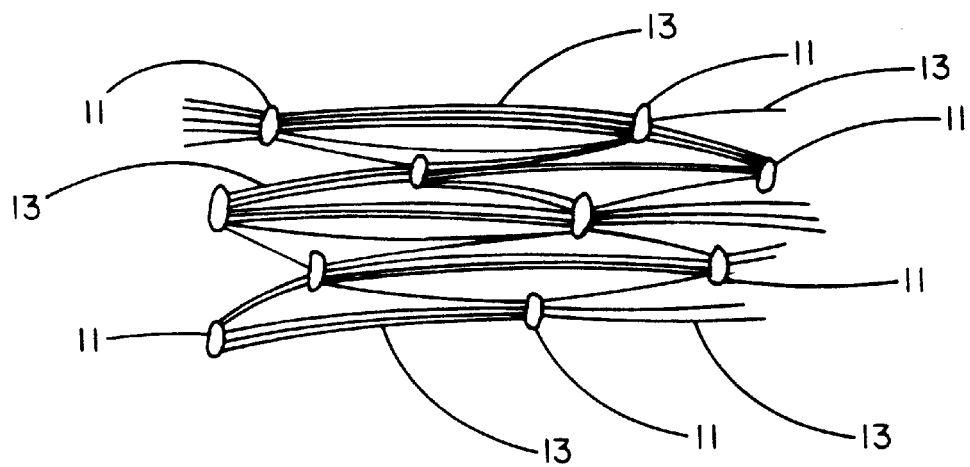
FIG. 1 describes an enlarged, schematic representation of the microstructure of the porous expanded PTFE film used to construct the intraluminal graft of the present invention.

As depicted by the enlarged, schematic representation of FIG. 1, these porous expanded PTFE films have a microstructure of nodes 11 interconnected by fibrils 13. These films are made by expansion by stretching in a single direction which is the direction in which the resulting fibrils are primarily oriented. As will be described, the intraluminal graft of the present invention is made of first and second layers of these films wherein the fibrils of the first layer are oriented parallel to the longitudinal axis of the intraluminal graft and the fibrils of the second layer are oriented substantially circumferential to the intraluminal graft.

The fibril lengths of the porous expanded PTFE films referred to herein were estimated mean values obtained by examining scanning electron photomicrographs of these films. The mean fibril lengths of the films used to construct the intraluminal grafts of the present invention are preferred to be within the range of about 5 to about 120 microns, although fibril lengths beyond this range may also be useful.

Figure 2:
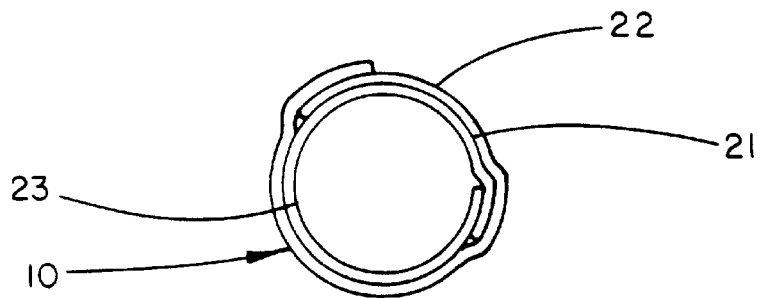
FIG. 2 describes a transverse cross section of the intraluminal graft of the present invention having at least one substantially longitudinally-oriented first layer and at least one substantially circumferentially-oriented second layer.
Figure 2A:
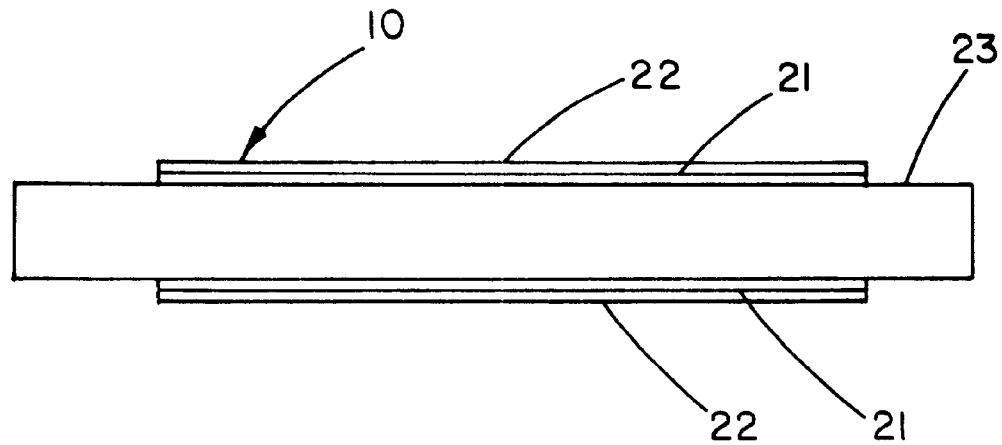
FIG. 2A describes a longitudinal cross section of the intraluminal graft of FIG. 2.

The intraluminal graft of the present invention is made by wrapping first and second layers of porous expanded PTFE film about a stainless steel mandrel of the same diameter as the desired diameter of the intraluminal graft. According to the embodiment described by the transverse cross section of FIG. 2 and the longitudinal cross section of FIG. 2A, the first layer 21 is first wrapped around the mandrel 23 with the fibrils of the film microstructure oriented longitudinally, that is, approximately parallel to the longitudinal longitudinally, that is, approximately parallel to the longitudinal axis of the mandrel and the intraluminal graft. The film should be of length at least equal to the desired length of the vascular graft, and of adequate width to allow the film to be fully wrapped around the mandrel surface thereby resulting in a tubular covering of longitudinally oriented film.

Figure 3:
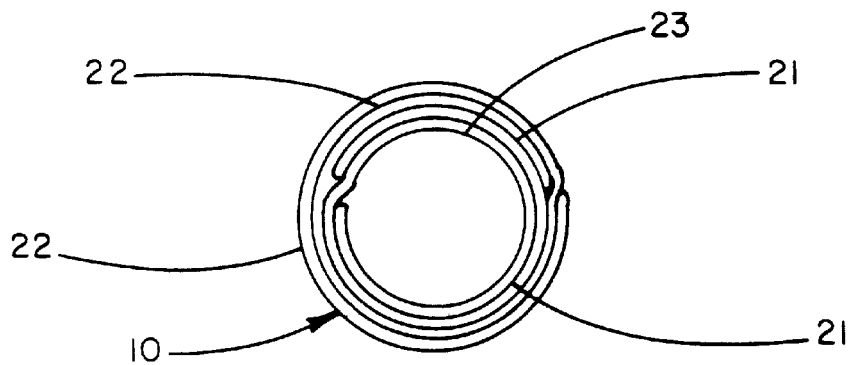
FIG. 3 describes a transverse cross section of the intraluminal graft of the present invention having at least two substantially longitudinally-oriented first layers and at least two substantially circumferentially-oriented second layers.
Figure 3A:
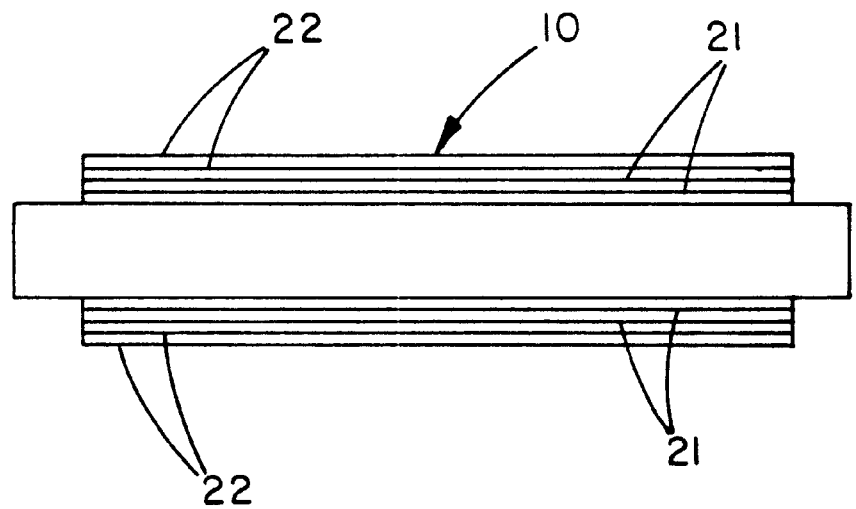
FIG. 3A describes a longitudinal cross section of the intraluminal graft of FIG. 3.

As described by the transverse cross section of FIG. 3 and the longitudinal cross section of FIG. 3A, the film of the first layer 21 may be of adequate width to allow wrapping at least twice around the surface of the mandrel L3 if desired, thereby resulting in at least two thicknesses of the first layer 21 of film.

The second layer 22 of film is then applied by wrapping porous expanded PTFE film circumferentially about the mandrel 23 and first layer 21 of film so that the fibrils of the microstructure of the second 22 layer are oriented substantially circumferentially around the mandrel 23 and first layer 21 of film. The second layer 22 of film should be of width at least equal to the desired length of the intraluminal graft 10. Again as shown by FIGS. 3 and 3A, the substantially circumferentially-oriented second layer 22 of film may be wrapped around the mandrel 23 and first layer 21 of film at least twice to provide for two or more thicknesses of film in the second layer.

Figure 4:
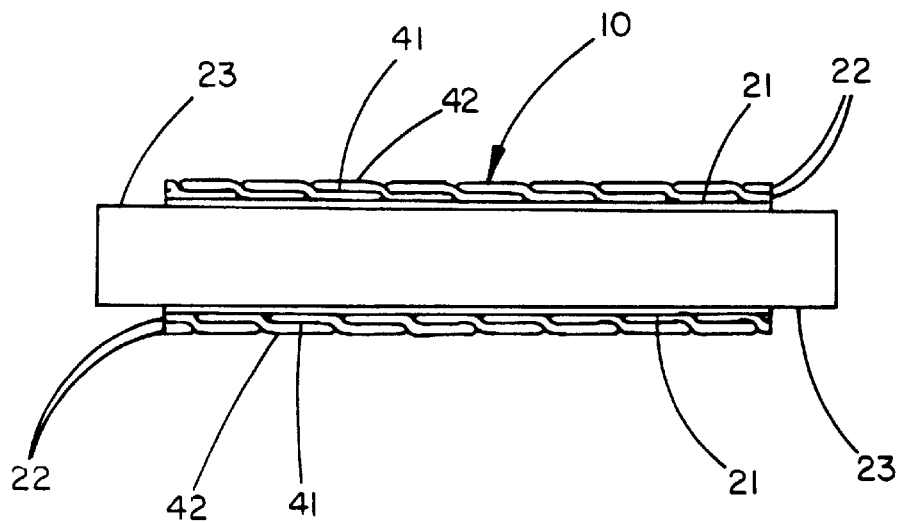
FIG. 4 describes an alternative embodiment of the intraluminal graft of FIG. 3 wherein the at least one substantially circumferentially-oriented second layer is a helically wrapped outer layer.

Alternatively, a narrower film may be used for the second layer 22 if the film is wrapped helically about the mandrel 23 as described by the longitudinal cross section of FIG. 4. In this case the helically-wrapped film may be applied with a pitch that allows each wrap 42 of film to preferably overlap at least half of the width of the preceding wrap 41, thereby resulting in a second layer 22 of film that includes at least two thicknesses of substantially circumferentially-oriented film. Conversely, if it is desired to minimize the wall thickness of the intraluminal graft then a minimum amount of overlap may be used.

Figure 5:
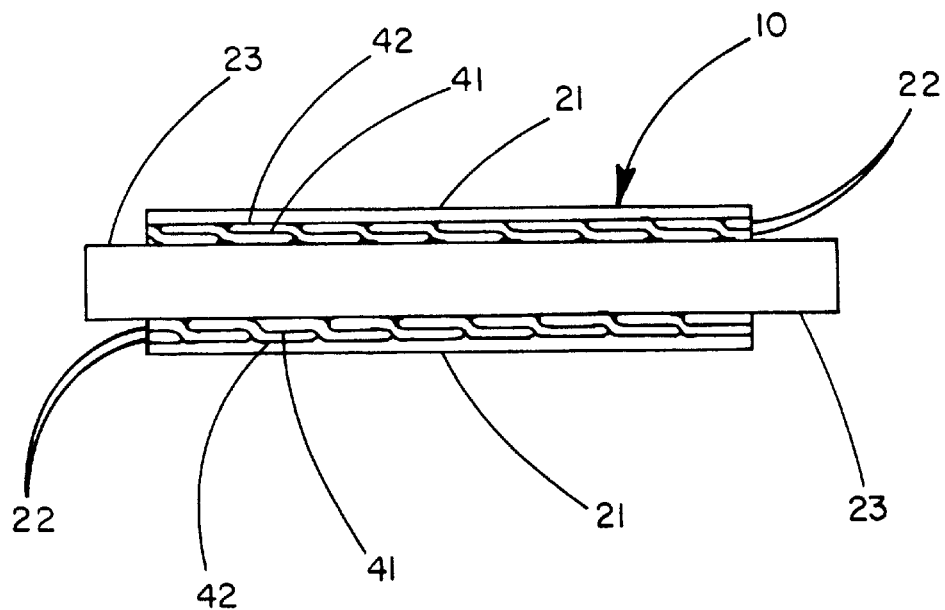
FIG. 5 describes an alternative embodiment of the intraluminal graft of FIG. 4 wherein the inner and outer relationships of the first and second layers are reversed.

If it is desired that the circumferentially-oriented second layer of film serve as the luminal surface of the graft, then the application sequence of the first and second layers must be reversed as shown by the longitudinal cross section of FIG. 5.

The mandrel with the first and second layers of film is then heated adequately to cause adjacent layers of film to thermally bond to each other while limiting the applied heat so as not to cause significant damage to the microstructure of the films. The mandrel and films are then allowed to cool and the resulting vascular graft is removed from the mandrel. The ends of the vascular graft may then be trimmed off square with a sharp blade if desired.

Alternatively, an adhesive may be used between the layers of PTFE film to adhere adjacent layers together. The PTFE film may be made with the adhesive on only one surface of the film. The adhesive coated films are oriented during wrapping of the mandrel so that the adhesive-coated side of the film contacts adjacent layers of film and does not contact the mandrel. The adhesive is preferably in the form of a discontinuous, porous coating in order to have a minimal effect on the porosity of the completed thin-wall intraluminal graft. The adhesive must be biocompatible; preferred adhesives are thermoplastics of lower melt point than the crystalline melt point of the PTFE film. Thermoplastic fluoropolymers such as FEP are most preferred. These types of adhesives are activated by placing the film-wrapped mandrel into an oven at a combination of time and temperature adequate to cause melting of the adhesive.

EXAMPLE 1

A thin-wall intraluminal graft was constructed by wrapping porous expanded PTFE film about an 8 mm diameter cylindrical stainless steel mandrel and then heating the film-wrapped mandrel. A 60 cm length of porous expanded PTFE film was wrapped around the surface of the mandrel with the fibrils of the film oriented parallel to the longitudinal axis of the mandrel. The film used was of about 0.03 mm thickness, 40 mm width, 40 micron fibril length, and about 0.3 g/cc density. The density of non-porous PTFE is about 2.2 g/cc; consequently the chosen film was about 86% porous. All film thickness measurements for each example were made with a Mitutoyo model no. 2804-10 snap gauge having a part no. 7300 frame, by placing a film sample between the measuring pads of the gauge and gently easing the pads into contact with the film sample until the pads were in full contact with the film sample under the full force of the spring-driven snap gauge. Film density values were based on the bulk volume of a film sample using the snap-gauge thickness measurement.

Figure 6:
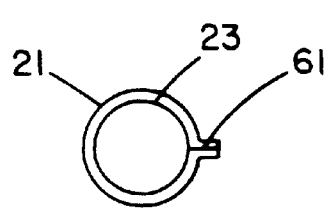
FIG. 6 describes a method of forming a seam with the edges of the first layer of film.

A flanged seam was formed as shown by the transverse cross section of FIG. 6; the contacting surfaces 61 of the flanged seam of the first layer 21 were heated with a hand-held iron by pressing the flanged seam between the iron and a sheet of polyimide film. The temperature of the heated surface of the iron was about 380° C. Excess film outside of the sealed portion of the seam was trimmed away with a scalpel blade and discarded.

Figure 6A:
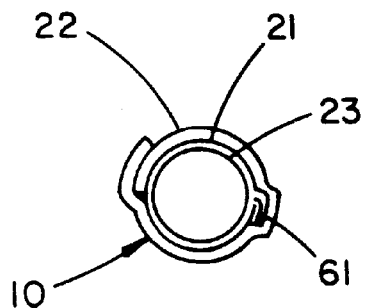
FIG. 6A describes fitting a second layer of film to the embodiment of FIG. 6.

As described by the transverse cross section of FIG. 6A, a second layer 22 of film was then applied about the surface of the first, longitudinally-oriented layer 21 by helically wrapping the second layer 22 over the surface of the first layer 21. The film used was of about 0.03 mm thickness, 12.5 mm width, 50 micron fibril length, and about 0.3 g/cc density. Each wrap 42 of the helically-oriented wrapping overlapped the adjacent wrap 41 by half of the width of the adjacent wrap 41 as depicted by FIG. 4. The mandrel 23 was first helically wrapped in one direction, followed by a second helical wrapping applied in the opposite direction which resulted in a total thickness of four layers of helically applied film. The mandrel 23 having the longitudinally-oriented first layer 21 and helically-oriented second layers 22 of film was then placed into an oven set at 385° C. for twenty minutes after which it was removed from the oven and allowed to cool. The heating process caused the helically oriented second layer 22 of film to shrink in a direction parallel to the direction of the fibrils, that is, circumferential to the surface of mandrel 23. The amount of heat used was adequate to cause adjacent contacting surfaces of the film to thermally bond together.

After the mandrel 23 was removed from the finished intraluminal graft 10, the wall thickness of the graft was measured by transversely cutting off a short length of graft, longitudinally slitting the tubular graft to form a sheet and then measuring the thickness of the sheet with the precision snap gauge. The thickness was determined to be about 0.07 mm. The mechanical integrity of a 10 cm long sample of this graft was challenged by inserting a latex balloon of 8 mm unpressurized diameter into the lumen of the sample and pressurizing the balloon with air at a pressure of 3.5 kg/cm$^2$ for 3 minutes. Inflation to this pressure required about five seconds of time which was not included in the 3 minute test time. This test caused no visible damage to the intraluminal graft.

EXAMPLE 2

Figure 7:
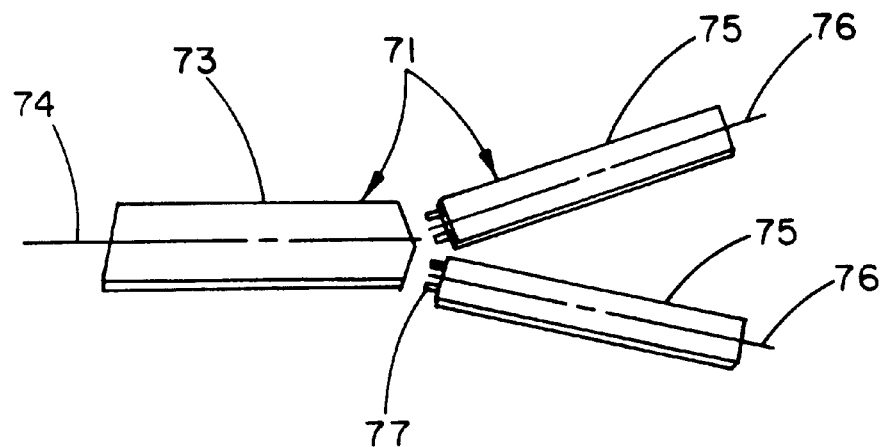
FIG. 7 describes a mandrel useful for constructing a bifurcated intraluminal graft of the present invention.

A bifurcated intraluminal graft was made by first constructing a flat mandrel 71 from 1.5 mm thick stainless steel as shown by FIG. 7; the mandrel 71 was cut into a Y-configuration wherein the trunk 73 was about 18 mm wide and legs 75 of the mandrel 71 were about 10 mm wide; the trunk 73 and legs 75 were each of about 80 mm length; the centerline 76 of each leg 75 diverged from the centerline 74 of the trunk 73 by an angle of about 15 degrees. The legs 75 were made as separate pieces and were retained to the trunk 73 in a removable fashion by the use of pins 77. All edges of the mandrel 71 were radiused.

The completed mandrel was placed between 2 layers of the same film used previously for the longitudinally-oriented film of Example 1. The fibrils of the layers of film were oriented parallel to the longitudinal axis of the trunk of the mandrel. The edges of the film were sealed together and trimmed around the perimeter of the flat mandrel in the same fashion as the edge of the longitudinally oriented film layer of Example 1.

Next, a helical wrapping of 12.5 mm wide film was applied by hand around the trunk and individual legs of the mandrel. The film used for the helical wrapping was a porous expanded PTFE film with an additional layer or coating of FEP on one surface. The FEP layer allows for subsequent thermal bonding of the film at a lower temperature than required for the PTFE-only film so that shrinkage of the PTFE film during the heating process may be substantially avoided.

The FEP-coated porous expanded PTFE film was made by a process which comprises the steps of:

a) contacting a porous PTFE substrate, usually in the form of a membrane or film, with another layer which is preferably a film of FEP or alternatively of another thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching and the thickness of the adhesive prior to stretching.

The FEP-coated porous expanded PTFE film used to make this example had a thickness of about 0.03 mm, a density of about 0.3 g/cc, a fibril length of about 80 microns, and a width of about 12.5 mm. This film used FEP as the continuous layer of thermoplastic fluoropolymer adhesive. The FEP-coated side of the film was placed against the layer of longitudinally-oriented film so that the FEP-coated side of the film faced the mandrel surface and the porous expanded PTFE side of the film faced outward away from the mandrel surface.

After helical wrapping with the FEP-coated film, the film-covered mandrel was placed into an oven set at 360° C. for 4 minutes. After removal from the oven, the assembly was allowed to cool. The sealed edges of film at the ends of the trunk and legs of the mandrel were trimmed away with a scalpel blade allowing the mandrel to be removed from the completed, bifurcated intraluminal graft by separating the legs from the trunk of the mandrel. The portion of the intraluminal graft between the legs was re-sealed with the hand iron to ensure the integrity of that region. The thickness of the wall of completed bifurcated intraluminal graft was measured to be about 0.10 mm.

EXAMPLE 3

A tubular intraluminal graft of the type described in Example 1 was constructed of a discontinuous FEP-coated film. Examination of the FEP-coated side of the film by scanning electron microscopy revealed FEP on only small portions of the nodes and fibrils at the surface of the film. It was estimated that less than 10% of the available node and fibril surface area exposed at the surface of the film was covered by FEP. The presence of the FEP adhesive thus had little or no adverse effect on the porosity of the porous PTFE layer of the film. This FEP-coated film was about 0.01 mm thick, of about 50 micron fibril length and has a density of about 0.3 g/cc.

Figure 8:
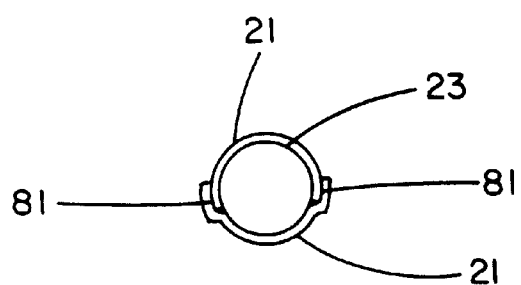
FIG. 8 describes an alternative method to that described by FIG. 6 for forming seams with the edges of the first layer of film.

The first layer 21 of film was applied by wrapping a 6 mm diameter cylindrical stainless steel mandrel 23 with two 12.5 mm wide strips of the FEP-coated porous expanded PTFE film as shown by the transverse cross section of FIG. 8. The edges 81 of the two layers of longitudinally-oriented film overlapped by about 3 mm. The PTFE side of the film was against the surface of the mandrel with the FEP coating facing away from the mandrel surface. The fibrils of the PTFE layer were oriented parallel to the longitudinal axis of the mandrel. A helically-wrapped second layer was then applied using a 12.5 mm wide strip of the same type of discontinuous FEP-coated film with the FEP-coated side of the film facing inward in contact with the FEP-coated surface of the longitudinally oriented layer. Each wrap of the helically-wrapped film overlapped three-quarters of the width of the previous wrap. The wrapping was applied in only one direction with the result that the helical wrapping was four layers thick due to the overlapping of the film during helical wrapping. The film-wrapped mandrel was then placed into an oven set at 325° C. for 20 minutes after which it was removed and allowed to cool. The mandrel was then removed from the completed intraluminal graft. The wall thickness of this example was determined to be about 0.06 mm.

EXAMPLE 4

Figure 9:
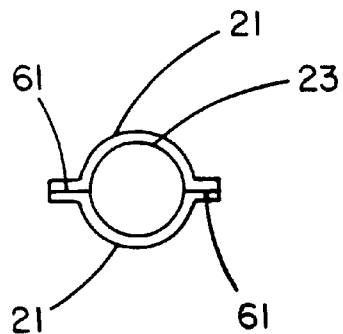
FIG. 9 describes an alternative method to that described by FIG. 8 for forming seams with the edges of the first layer of film.

A thin-wall intraluminal graft was constructed by wrapping porous expanded PTFE film about a 6 mm diameter cylindrical stainless steel mandrel and then heating the film-wrapped mandrel. As described by the transverse cross section of FIG. 9, a first layer 21 of film was formed by wrapping two 120 cm lengths of porous expanded PTFE film around the surface of the mandrel 23 with the fibrils of the film oriented parallel to the longitudinal axis of the mandrel, forming flanged seams 61. The film used was of about 0.01 mm thickness, 12.5 mm width, 50 micron fibril length, and about 0.3 g/cc density. This film did not have an FEP coating. The flanged seams were heat-sealed and trimmed in a fashion similar to that described in Example 1.

Figure 9A:
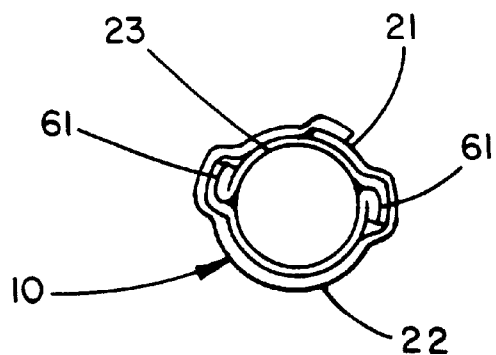
FIG. 9A describes fitting a second layer of film to the embodiment of FIG. 9.

As shown by the transverse cross section of FIG. 9A, a second layer 22 of the same film was then applied about the surface of the first, longitudinally-oriented layer 21 by helically wrapping the second layer 22 over the surface of the first layer 21. Each wrap of the helical wrapping overlapped the adjacent wrap by about 1 mm. The mandrel was helically wrapped in one direction only. This resulted in a thickness of one layer of helically applied film as measured at any transverse cross section, except for the 1 mm wide overlapped areas which were two layers in thickness. The mandrel having the longitudinally and helically-oriented coverings of film was then placed into an oven set at 383° C. for 15 minutes after which it was removed from the oven and allowed to cool. The heating process caused the helically-oriented film to shrink in a direction parallel to the direction of the fibrils, that is, circumferential to the mandrel surface. The amount of heat used was adequate to cause adjacent contacting surfaces of the film to thermally bond together.

The wall thickness of the finished intraluminal graft was determined to be 0.033 mm where adjacent helical layers overlapped and 0.025 mm between overlapped edges. The mechanical integrity of a 12 cm long sample of this graft was challenged by inserting a latex balloon of about 6 mm outside diameter into the lumen of the sample and pressurizing the balloon with air at a pressure of 1 kg/cm$^2$ for 3 minutes. Inflation to this pressure required about three seconds of time which was not included in the 3 minute test time. This test caused no visible damage to the intraluminal graft.

EXAMPLE 5

Figure 10:
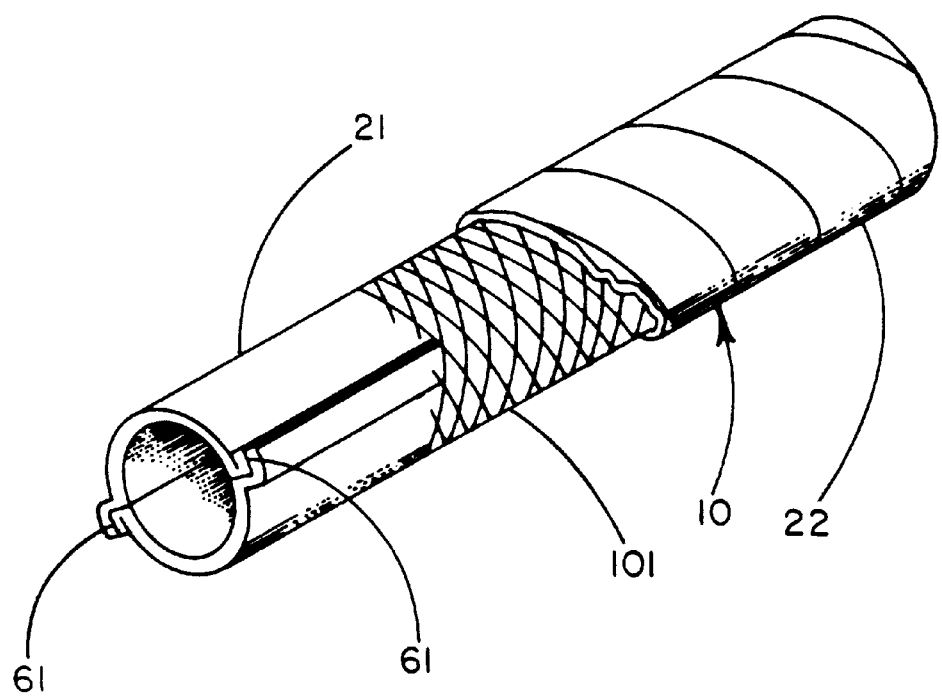
FIG. 10 describes an alternative embodiment of the intraluminal graft of the present invention incorporating a braided reinforcing layer.

As shown by the cutaway perspective view of FIG. 10, a thin-wall intraluminal graft 10 incorporating a layer of braided reinforcing material 101 was made by first applying a first layer 21 of film to a 6 mm stainless steel mandrel using the same method and the same 12.5 mm wide film described by Example 4. A roll of the same film used to form the first layer 21 was cut to a width of 6.2 mm. The resulting roll of narrow film was then paid off onto 8 individual small spools. The process of paying the film from the supply roll onto the small spools used enough tension that the narrow film bunched down into a flat thread of about 0.8 mm width and 0.03 mm thickness. This bunching of the porous expanded PTFE film into a thread occurred without any appreciable increase in length. The small spools were then used as supply spools on a Steeger model D-5600 braiding machine to form a braid from the thread on the exterior surface of the film-covered mandrel. The braid density was about 5 picks per cm. After braiding, a helically wrapped second layer 22 of the same film used for the first layer 21 of this example was applied. The helical wrapping was applied so that each wrap overlapped the edge of the previous wrap by about 2 mm. The braided and film-wrapped mandrel was then placed into an oven set at 383° C. for a period of 15 minutes, removed and allowed to cool. After removal of the mandrel from the finished length intraluminal graft, the wall thickness of this graft was determined to be 0.06 mm. The mechanical integrity of a 12 cm long sample of this graft was challenged by inserting a latex balloon of 6 mm outside diameter into the lumen of the sample and pressurizing the balloon with air at a pressure of 3.5 kg/cm² for 3 minutes. Inflation to this pressure required about five seconds of time which was not included in the 3 minute test time. This test caused no visible damage to the intraluminal graft.

It is apparent that the foregoing examples are illustrative only and that the sequence, number and characteristics of the various layers of the intraluminal graft may be changed as desired.

Figure 11A:
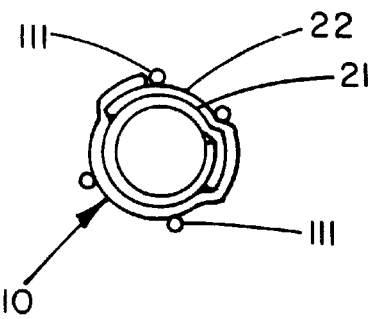
FIGS. 11A, 11B, 11C, 11D and 11E describe views of the intraluminal graft incorporating alternative reinforcing components.
Figure 11B:
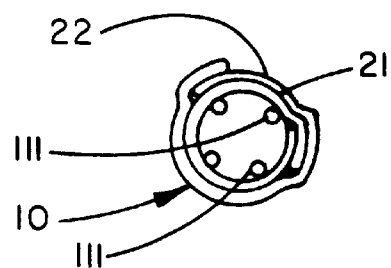
Figure 11C:
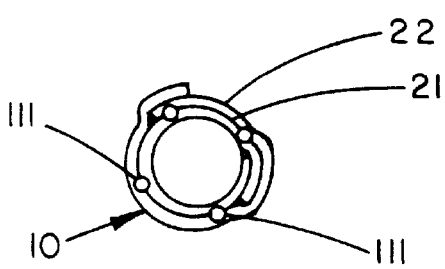
Figure 11D:
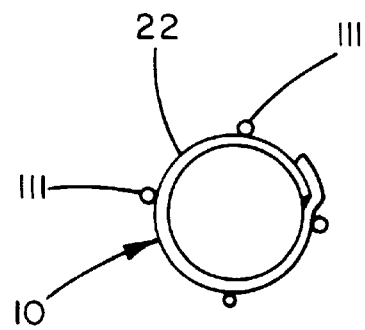

As previously described, the intraluminal graft may be provided with substantially longitudinally-oriented reinforcing ribs in the form of stringers of, for example, FEP or PTFE. The ribs are not limited to being oriented parallel to the longitudinal axis of the intraluminal graft, but may also be provided with a helical bias. FIG. 11A describes a cross sectional view of an intraluminal graft 10 with ribs 111 on the exterior surface. FIG. 11B describes a cross sectional view of an intraluminal graft 10 with ribs 111 on the luminal surface. FIG. 11C shows a cross sectional view having ribs 111 between two layers of film 21 and 22.

Figure 11E:
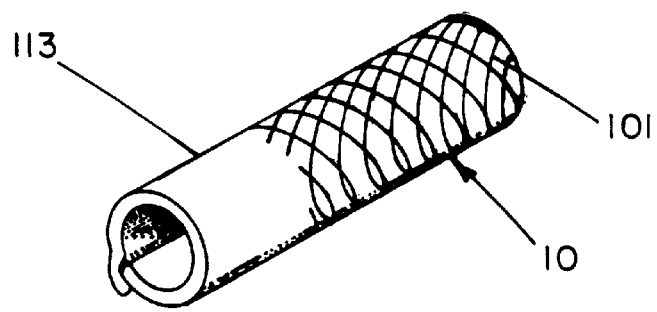

For the intraluminal graft of the present invention, either the first or the second layer of porous expanded PTFE film may be replaced by alternative reinforcing components such as a braid or at least one reinforcing rib. If at least one reinforcing rib is used, the orientation of the at least one rib should be substantially perpendicular to the orientation of the fibrils within the film layer. For example, as shown by FIG. 1D, the intraluminal graft 10 may comprise at least one layer of porous expanded PTFE film 22 having fibrils oriented substantially circumferential to the intraluminal graft and also have at least one substantially longitudinally-oriented reinforcing rib 111 on the exterior surface of film 22. Further, as shown by the perspective view of FIG. 11E, the intraluminal graft may also be provided with an alternative reinforcing component in the form of a braid 101 on the exterior surface of the film 113 wherein the film fibrils may be oriented either substantially longitudinal or substantially circumferential. Conversely, the braid 101 or substantially longitudinally-oriented reinforcing ribs 111 may be provided on the luminal surface of the intraluminal graft 10.

Likewise, at least one layer of porous expanded PTFE film having fibrils oriented to be substantially parallel to the longitudinal axis of the intraluminal graft may also be provided with a reinforcing braid or at least one reinforcing rib. For this embodiment, the orientation of the at least one reinforcing rib should be circumferential or helical. The at least one reinforcing rib may therefore be a single helically oriented reinforcing rib. These reinforcing components may be provided on either the exterior or luminal surfaces.

For embodiments wherein one of the layers of porous PTFE film is replaced by an alternative reinforcing component in the form of a braid or at least one reinforcing rib, the thickness of the film layer does not include the thickness of the alternative reinforcing component.

We claim:

1. An intraluminal graft comprising a tube having:
    a) an inner layer comprised of porous PTFE film having a microstructure comprised of fibrils, said fibrils being substantially parallel to one another;
    b) an outer layer concentrically covering said inner layer, said outer layer comprised of porous PTFE film having a microstructure comprised of fibrils, said fibrils being substantially parallel to one another and substantially perpendicular to the fibrils of the inner layer; and
    c) a wall thickness of less than about 0.25 mm.

2. The graft of claim 1 in which said inner layer is formed from helically wrapped film.

3. The graft of claim 2 in which the wall thickness is less than 0.10 mm.

4. The graft of claim 3 in which the wall thickness is less than 0.06 mm.

5. The graft of claim 1 in which said outer layer is helically wrapped around said inner layer.

6. The graft of claim 5 in which the wall thickness is less than 0.10 mm.

7. The graft of claim 6 in which the wall thickness is less than 0.06 mm.

8. The graft of claim 1 in which said inner layer and said outer layer are formed from helically wrapped film.

9. The graft of claim 8 in which the wall thickness is less than 0.10 mm.

10. The graft of claim 9 in which the wall thickness is less than 0.06 mm.

11. The graft of claim 1 in which said inner layer is attached to said outer layer by an adhesive.

12. The graft of claim 11 wherein the adhesive is a thermoplastic fluoropolymer.

13. The graft of claim 12 wherein the thermoplastic fluoropolymer is fluorinated ethylene propylene.

14. The graft of claim 13 wherein the fluorinated ethylene propylene is porous.

15. The graft of claim 11 wherein the adhesive is porous.

16. The graft of claim 11 wherein the adhesive is non-porous.

17. The graft of claim 1 in which the wall thickness is less than 0.10 mm.

18. The graft of claim 17 in which the wall thickness is less than 0.06 mm.

19. The graft of claim 1 having a reinforcing material between said inner layer and said outer layer.

20. The graft of claim 19 in which the reinforcing material is braided.

21. The graft of claim 1 comprising a bifurcated graft.

22. The graft of claim 1 wherein said graft incorporates at least one reinforcing rib.

23. The graft of claim 1 wherein the intraluminal graft has a longitudinal axis and wherein the fibrils of the inner porous polytetrafluoroethylene layer are substantially parallel to the longitudinal axis.

24. The graft of claim 23 in which the wall thickness is less than 0.10 mm.

25. The graft of claim 24 in which the wall thickness is less than 0.06 mm.

26. The graft of claim 1 in which said inner layer is attached to said outer layer by heat bonding.

\* \* \* \* \*